United States Patent [19]

Kojima et al.

[11] Patent Number: 4,544,633
[45] Date of Patent: Oct. 1, 1985

[54] PROCESS FOR PRODUCING VITAMIN $B_{12}$ BY THE FERMENTATION TECHNIQUE, AND VITAMIN $B_{12}$-PRODUCING MICROORGANISM

[75] Inventors: Ichiro Kojima, Yokosuka; Kouji Komiya, Yokohama; Hiroshi Sato, Kawasaki; Yutaka Oguchi, Tokyo, all of Japan

[73] Assignee: Nippon Oil Company, Ltd., Tokyo, Japan

[21] Appl. No.: 468,996

[22] Filed: Feb. 23, 1983

[30] Foreign Application Priority Data

Feb. 26, 1982 [JP] Japan .................................. 57-29064
Feb. 26, 1982 [JP] Japan .................................. 57-29065
Feb. 26, 1982 [JP] Japan .................................. 57-29066

[51] Int. Cl.[4] .......................... C12P 19/42; C12N 1/20
[52] U.S. Cl. ......................................... 435/86; 435/253
[58] Field of Search .................................. 435/86, 253

[56] References Cited

U.S. PATENT DOCUMENTS 3,043,750 7/1962 Becher et al. .......................... 435/86
3,062,723 11/1962 Dobry et al. .......................... 435/86
3,411,991 11/1968 Lim ...................................... 435/86

Primary Examiner—Sam Rosen
Attorney, Agent, or Firm—Wenderoth, Lind & Ponack

[57] ABSTRACT

A process for producing vitamin $B_{12}$ by the fermentation technique which comprises cultivating a vitamin $B_{12}$-producing microorganism belonging to the genus Propionibacterium in a culture medium containing a carbon source and a nitrogen source, and collecting vitamin $B_{12}$ accumulated in the cells of the microorganism; characterized in that (1) the cultivation is carried out while adding an alkali at suitable times to the cultivation system so that during the cultivation, the cultivation system is maintained at a pH in the range of about 5 to about 7.5, and
(2) the cultivation is carried out while adding a carbon source portionwise to the cultivation system nearly at the same time as the addition of the alkali,
(3) provided that when a vitamin $B_{12}$-producing microorganism having resistance to propionic acid is used as the microorganism, the portionwise addition of the carbon source in (2) can be omitted. Also disclosed are propionic acid-resistant, vitamin $B_{12}$-producing microorganism of the genus Propionibacterium.

12 Claims, No Drawings

PROCESS FOR PRODUCING VITAMIN $B_{12}$ BY THE FERMENTATION TECHNIQUE, AND VITAMIN $B_{12}$-PRODUCING MICROORGANISM

This invention relates to an improved process for producing vitamin $B_{12}$ in a markedly increased output by an industrially easy operation. The invention also relates to a vitamin $B_{12}$-producing microorganism having resistance to propionic acid, which can be used in the process.

More specifically, this invention relates to a process for producing vitamin $B_{12}$ by the fermentation technique which comprises cultivating a vitamin $B_{12}$-producing microoganism belonging to the genus Propionibacterium in a culture medium containing a carbon source and a nitrogen source, and collecting vitamin $B_{12}$ accumulated in the cells of the microorganism; characterized in that (1) the cultivation is carried out while adding an alkali at suitable times to the cultivation system so that during the cultivation, the cultivation system is maintained at a pH in the range of about 5 to about 7.5, and
(2) the cultivation is carried out while adding the carbon source portionwise to the cultivation system nearly at the same time as the addition of the alkali,
(3) provided that when a vitamin $B_{12}$-producing microorganism having resistance to propionic acid is used as the microorganism, the portionwise addition of the carbon source in (2) can be omitted.

This invention also relates to a vitamin $B_{12}$-producing microorganism having resistance to propionic acid which is not described in the literature and which can be used in the aforesaid process; and also to a process for producing the microorganism.

A process for producing vitamin $B_{12}$ has previously been known which comprises cultivating a vitamin $B_{12}$-producing microorganism, for example a vitamin $B_{12}$-producing microorganism of the genus Propionibacterium, in a culture medium containing a carbon source and a nitrogen source, and collecting vitamin $B_{12}$ accumulated in the microbial cells (for example, U.S. Pat. No. 2,951,017).

The present inventors conducted investigations in order to improve the output of vitamin $B_{12}$ in the aforesaid manufacturing process, and found that in the production of vitamin $B_{12}$ by the fermentation technique using a vitamin $B_{12}$-producing microorganism belonging to the genus Propionibacterium, the concentration of the carbon source in the cultivation system acts as an important factor on changes in the amount of vitamin $B_{12}$ accumulated in the microbial cells during the cultivation.

Further investigations led to the discovery that by performing cultivation while adding an alkali at suitable times to the cultivation system according to changes in the pH of the system so as to maintain the pH of the system at about 5 to about 7.5 during the cultivation, and while adding the carbon source portionwise to the cultivation system nearly at the same time as the addition of the alkali, vitamin $B_{12}$ can be produced with industrial advantage in an amount two times or more as large as in the case of performing the cultivation by adding all the carbon source to the culture medium in the initial stage of cultivation. This will be shown hereinbelow by Examples and Comparative Examples.

It has also been found that in the production of vitamin $B_{12}$ by the fermentation technique using a vitamin $B_{12}$-producing microorganism of the genus Propionibacterium, a hydrolyzate of spent molasses obtained by hydrolyzing spent molasses, which is used with difficulty by the vitamin $B_{12}$-producing microorganism of the genus Propionibacterium, is useful as a carbon source which can markedly increase the amount of vitamin $B_{12}$ accumulated in the cells of the vitamin $B_{12}$-producing microorganism of the genus Propionibacterium to two times or more.

Further investigations show that fructose contained in the hydrolyzate of spent molasses takes part in increasing the amount of vitamin $B_{12}$ accumulated, and the increasing effect is not interfered with by the copresence of glucose in the hydrolyzate. It has also been found that fructose can be utilized instead of the hydrolyzate, and the aforesaid increasing effect of fructose is not interfered with even if a part, particularly up to nearly one-half, of the fructose is replaced by cheaper glucose.

It has further been found that the hydrolyzate of spent molasses available at low cost gives better results presumably because some other component of the hydrolyzate of molasses acts cooperatively with fructose and glucose, and this, coupled with the utilizability of the hydrolyzate of molasses as a carbon source whose cost is about one-third of the entire cost of production of vitamin $B_{12}$ by the fermentation technique, further increases the industrial value of the process of this invention.

The present inventors found that in the production of vitamin $B_{12}$ by the fermentation technique using conventional vitamin $B_{12}$-producing microorganisms of the genus Propionibacterium, the growth of the vitamin $B_{12}$-producing microorganism sometimes stops during the cultivation and the production of vitamin $B_{12}$ fails. Investigations have shown that during the cultivation, propionic acid formed in the cultivation system gradually builds up and increases in amount, and when the amount of propionic acid accumulated in the cultivation system exceeds a certain limit, the growth of the vitamin $B_{12}$-producing microorganism is inhibited until finally its growth stops and the production of vitamin $B_{12}$ ceases.

The present inventors continued their investigations in order to avoid this problem in the production of vitamin $B_{12}$ by the fermentation technique using vitamin $B_{12}$-producing microorganisms of the genus Propionibacterium, and to develop a process which can give vitamin $B_{12}$ in an improved output.

These investigations have led to the discovery that a microorganism strain having resistance to propionic acid and being capable of producing vitamin $B_{12}$ in markedly improved output can be created by subjecting a vitamin $B_{12}$-producing parental microorganism strain of the genus Propionibacterium to a combination of artificial mutation-inducing treatment and natural mutation-inducing treatment. It has also been found that the resultant microorganism strain can be cultivated under the same cultivation conditions as for the parental strain without the need for any special cultivation conditions, and can produce vitamin $B_{12}$ in an output two or more times that of vitamin $B_{12}$ produced by the parental strain. The cultivation is preferably carried out under the condition (1) above, more preferably under the conditions (1) and (2) above.

It is an object of this invention to provide an improved process for producing vitamin $B_{12}$ by the fermentation technique using a vitamin $B_{12}$-producing microorganism of the genus Propionibacterium.

This and other objects and advantages of this invention will become more apparent from the following description.

In the process of this invention, a vitamin $B_{12}$-producing microorganism of the genus Propionibacterium is used. Examples of such a vitamin $B_{12}$-producing microorganism include *Propionibacterium shermanii* IFO 12391 and IFO 12426 [Institute for Fermentation, Osaka, Japan] and *Propionibacterium freudenreichii* IFO 12424 [Institute for Fermentation, Osaka, Japan], which are freely distributable known strains. Other usable vitamin $B_{12}$-producing strains include *Propionibacterium shermanii* NOC 11011 having imparted thereto the property of easily sedimenting [FERM BP-85; Fermentation Research Institute, Agency of Industrial Science and Technology, Japan; the strain deposited internationally under the Budapest Treaty], *Propionibacterium shermanii* NOC 11012 having imparted thereto resistance to propionic acid [FERM BP-86; Fermentation Research Institute, Agency of Industrial Science and Technology, Japan; the strain deposited internationally under the Budapest Treaty], and *Propionibacterium freudenreichii* NOC 11013 having imparted thereto resistance to propionic acid [FERM BP-87; the strain deposited internationally under the Budapest Treaty].

The microbiological properties of the *Propionibacterium shermanii* are the same as the known properties of the parental strain except that its rate of sedimentation is faster than that of the parental strain *Propionibacterium shermanii* IFO 12391 when the cultivation system is left to stand. The microbiological properties of the *Propionibacterium shermanii* NOC 11012 are the same as the known properties of the parental strain *Propionibacterium shermanii* IFO 12391 except that it has greater resistance to propionic acid. The microbiological properties of the *Propionibacterium freudenreichii* NOC 11013 are the same as the known properties of the parental strain *Propionibacterium freudenreichii* IFO 12424 except that it has greater resistance to propionic acid. The microbiological properties of these parental strains are described, for example, in Bergy's Manual of Determinative Bacteriology, 8th edition.

The above-mentioned *Propionibacterium shermanii* NOC 11011 (FERM BP-85) can be derived from the parental strain *Propionibacterium shermanii* IFO 12391 by utilizing a mutant-forming procedure with ultraviolet irradiation. One example of this is shown in Referential Example 1 given hereinbelow.

The vitamin $B_{12}$-producing microorganism belonging to the genus Propionibacterium having resistance to propionic acid as exemplified above can be produced, for example by a process which comprises subjecting a vitamin $B_{12}$-producing parent strain of the genus Propionibacterium to an artificial mutation-inducing treatment, and subjecting the surviving treated strain to a natural mutation-inducing treatment wherein the treated strain is cultivated in a liquid culture medium containing a carbon source, a nitrogen source and propionic acid, the concentration of propionic acid being above the minumum concentration at which propionic acid inhibits the growth of the parental strain. The natural mutation-inducing treatment is repeated until the amount of vitamin $B_{12}$ reaches at least about 1.5 times that of vitamin $B_{12}$ produced by the parental strain under the same cultivation conditions.

The parental strain may, for example, be *Propionibacterium shermanii* (for example, IFO 12391 and IFO 12426 strains), *Propionibacterium freudenreichii* (for example, IFO 12424 strain), and *Propionibacterium shermanii* NOC 11011 (for example, FERM BP-85 strain), which have already been cited hereinabove.

The vitamin $B_{12}$-producing microorganism of the genus Propionibacterium having resistance to propionic acid can be created by subjecting a vitamin $B_{12}$-producing parental strain of the genus Propionibacterium as exemplified above to an artificial mutation-inducing treatment and then subjecting the treated strain to the natural mutation-inducing treatment described above.

Means for artificial mutation-inducing treatment are known per se and can be utilized in this invention. Examples of such treating means include irradiation of artificial mutation-inducing rays such as ultraviolet rays, X-rays and radioactive rays (e.g., cobalt 60), and treatment with an artificial mutation-inducing agent such as nitrosoguanidine, hydroxylamine and 2-aminopurine. Treating conditions for the irradiation treatment, such as the dose and time, can be properly selected. For example ultraviolet rays can be irradiated in a dose of 300 erg/mm$^2$ for 2 minutes. Treating conditions for the treatment with inducing agents, such as the amount of the inducing agent and the treating time, can also be properly selected. For example, the parental strain can be treated with nitrosoguanidine in a concentration of 100 mg/liter for 30 minutes.

In the present invention, the treated strain surviving after the artificial mutation-inducing treatment is subjected to a natural mutation-inducing treatment wherein the treated strain is cultivated in a liquid culture medium containing not only a carbon source and a nitrogen source but also propionic acid in a concentration above the minimum concentration at which propionic acid inhibits the growth of the parental strain. The natural mutation-inducing treatment is repeatedly carried out until the amount of vitamin $B_{12}$ produced by the created propionic acid-resistant, vitamin $B_{12}$-producing strain reaches at least 1.5 times that of vitamin $B_{12}$ produced by the parental strain under the same cultivation conditions.

The minimum growth inhibitory concentration for the parental strain differs depending upon the kind of the parental strain used, but is about 10 g/liter of culture medium. In the present invention, a culture medium containing propionic acid in a concentration above the minimum growth inhibitory concentration, for example, about 10 to about 30 g/liter of culture medium, preferably about 15 to about 25 g/liter of culture medium is utilized. The number of repetitions of the natural mutation-inducing treatment is usually about 5 to about 20, and this can lead to the creation of a propionic acid-resistant, vitamin $B_{12}$-producing strain which will produce vitamin $B_{12}$ in the desired amount. The repeated cultivation is carried out by collecting colonies well grown on a propionic acid-containing liquid medium in the first cultivation, inoculating them in a separately prepared propionic acid-containing liquid medium and cultivating them there, then collecting colonies well grown on the second propionic acid-containing liquid medium and inoculating and cultivating them in a separately prepared propionic acid-containing liquid medium for the third time, and repeating the above cultivation procedure. The repeated cultivation may also be carried out in culture media which have a progressively increasing content of propionic acid as the number of the cultivation cycles increases.

One embodiment of producing the propionic acid-resistant, vitamin $B_{12}$-producing microorganism is given below in some detail. For example, 100 colonies of the treated strain surviving after the aforesaid artificial mutation-inducing treatment are cultivated for the first time in a liquid medium containing 20 g/liter of propionic acid for 5 days. Fifty treated strains are selected in the order of good growth determined by measuring the amount of growth at an optical density of 610 nm. The selected fifty strains are cultivated for the second time in a liquid culture medium containing 20 g/liter of propionic acid for 5 days. Likewise, 25 treated strains are selected in the same way and cultivated for the third time for 5 days. In this way, the cultivation can be repeated. During the repetition of cultivation, a mutant having resistance to propionic acid is derived and accumulated. The cultivation is repeated until finally the strain can be equivalently grown, for example both in a liquid medium containing 20 g/liter of propionic acid and a liquid medium containing no propionic acid. The resulting mutant can be separated as a propionic acid-resistant strain.

Known culture media and cultivation conditions can be used in this invention for cultivating vitamin $B_{12}$-producing microorganisms of the genus Propionibacterium including the aforesaid propionic acid-resistant, vitamin $B_{12}$-producing microorganisms.

The culture medium which can be used in this invention contains a carbon source and a nitrogen source and if required, minerals, vitamins, vitamin $B_{12}$-constituting components, etc. Examples of the carbon source are carbohydrates, sugars, organic acids, and alcohols. Specific examples are glucose, fructose, mannose, galactose, lactic acid, tartaric acid and glycerol. They can be used in suitable combinations. Examples of the nitrogen source are ammonium salts, nitric acid salts, peptone, yeast extract, casein, meat extract, corn steep liquor, urea, soybean residue, fish residues, and fermentation wastes.

Examples of the other components of the culture medium include vitamin $B_{12}$-constituting components such as 5,6-dimethylbenzimidazole, minerals such as phosphates, magnesium salts, potassium salts, calcium salts, manganese salts, cobalt salts, iron salts, zinc salts, molybdenum salts, copper salts and aluminum salts, and vitamins such as pantothenic acid.

The cultivation can be carried out under anaerobic conditions, and this is desirable. Preferably, stationary cultivation, and aeration-agitation cultivation with $N_2$ gas or $CO_2$ gas can be employed. The cultivation temperature is, for example, about 25° C. to about 37° C., and the cultivation time is, for example, about 3 days to about 10 days.

According to the process of this invention the vitamin $B_{12}$-producing microorganism of the genus Propionibacterium is cultivated in a culture medium at least containing a carbon source and a nitrogen source under the following conditions (1) to (3):

(1) the cultivation is carried out while adding an alkali at suitable times (at which the pH of the cultivation system can be adjusted to the values shown below) to the cultivation system so that during the cultivation, the cultivation system is maintained at a pH in the range of about 5 to about 7.5, preferably about 6 to about 7; and (2) the cultivation is carried out while adding the carbon source portionwise to the cultivation system nearly at the same time as the addition of the alkali (simultaneously or at a time up to about 10 minutes earlier or later than the addition of the alkali);

(3) provided that when the vitamin $B_{12}$-producing microorganism having resistance to propionic acid as described hereinabove is used as the microorganism, the portionwise addition of the carbon source set out in (2) can be omitted.

Examples of the alkali used for pH adjustment in (1) above include sodium hydroxide, potassium hydroxide, sodium carbonate, calcium hydroxide, and aqueous ammonia. They may be used either singly or as a mixture.

The amount of the carbon source added in (2) above is preferably about 50 to about 300 g, more preferably about 70 to about 200 g, per gram equivalent of the alkali added in (1).

The kind of the carbon source to be added portionwise can be properly selected, but preferably it is at least one carbon source selected from the group consisting of carbohydrates, sugars and alcohols. Sugars such as glucose, fructose and converted sugar are preferred. The amount of the carbon source to be added portionwise is preferably such that the concentration of the residual carbon source in the cultivation system does not exceed about 60 g/liter, more preferably about 50 g/liter (for example, the concentration of the residual carbon source in the cultivation system can be maintained at about 5 g/liter to about 30 g/liter of culture medium).

The amount of the residual carbon source in the cultivation system can be determined by an analytical method suited for the respective carbon source.

In the practice of the process of this invention, the portionwise addition of the carbon source in (2) is effected nearly at the same time as the addition of the pH-adjusting alkali to the cultivation system in (1). In other words, it may be effected simultaneously, or at some earlier or later time. If the time of adding the pH-adjusting alkali in (1) differs substantially from the time of adding the carbon source in (2), the growth of the microorganism is hampered, and the amount of vitamin $B_{12}$ produced is reduced, making it impossible to achieve the improved process of this invention.

Various means can be employed for effecting the addition of the pH-adjusting alkali in (1) and the portionwise addition of the carbon source in (2) nearly at the same time. For industrial practice, it is preferably effected by operating an alkali supplying pump for the alkali addition in (1) and a carbon source supplying pump for the addition of the carbon source in (2) in co-acting relationship. For example, it can be performed by operating a carbon source supplying pump in relation to the motion of an alkali supplying pump equipped with an automatic pH control means which is designed so that when it detects a change in the pH of the cultivation system and when the pH of the cultivation system shifts to an acidic side from a predetermined pH value, it actuates the alkali supply pump according to the change in pH. Other means can be utilized which make possible the substantially simultaneous addition of the alkali and the carbon source.

Preferred carbon sources added in (2) in this invention are fructose, a fructose-containing carbon source, a mixture of fructose and glucose, and a carbon source containing fructose and glucose. A hydrolysis product of spent molasses containing fructose and glucose is an industrially advantageous example of the carbon source.

Spent molasses are a by-product of the sugar manufacturing industry. When a procedure is used of concentrating sugarcane or beet juice as a sugar-making material and collecting the resulting sugar crystals, the contents of non-sugar organic materials, inverted sugar and salts in the mother liquor increase and its viscosity becomes higher, until finally no more sugar can be economically obtained. Molasses are a syrupy blackish brown by-product left at this time. In the present invention, a hydrolysis product of such spent molasses, fructose produced by any desired method, and a mixture of fructose and glucose obtained by replacing a part (preferably up to about 50% by weight) of fructose by cheap glucose can be utilized as the carbon source.

Hydrolysis of spent molasses can be performed by adding an inorganic acid such as hydrochloric acid or sulfuric acid to a syrupy liquid of the spent molasses or its aqueous dilution so that the pH of the liquid becomes about 1 to about 4, and heating the mixture at about 60° to 120° C. to induce hydrolysis. The treating time can be suitably selected, for example, about 10 to about 30 minutes.

Alternatively the hydrolysis can be effected by using an inverting enzyme, invertase. For example, enzyme invertase is added in an amount of about 0.05 to about 0.5% based on the weight of the spent molasses, and the molasses are subjected to inverting treatment at a pH of about 3 to 6 and a temperature of about 20° to about 60° C. The treating time can be properly chosen, for example about 2 to about 24 hours.

According to the process of this invention, the vitamin $B_{12}$-producing strain of the genus Propionibacterium is cultivated in a culture medium at least containing a carbon source and a nitrogen source under conditions (1) and (2), i.e. (1) while adding an alkali at suitable times to the cultivation system so that during the cultivation, the pH of the cultivation system is maintained at a pH in the range of about 5 to about 7.5, and (2) while adding the carbon source portionwise to the cultivation system almost at the same time as the addition of the alkali. Then, vitamin $B_{12}$ accumulated in the microbial cells in the culture broth are collected. Thus, vitamin $B_{12}$ can be produced by the fermentation technique in an improved output. The aforesaid condition (2) can be omitted when a propionic acid-resistant, vitamin $B_{12}$-producing microorganism is used as the vitamin $B_{12}$-producing microorganism.

Collection of vitamin $B_{12}$ can be carried out by separating the microbial cells from the culture broth by centrifugal separation, for example, and separating and recovering vitamin $B_{12}$ from the microbial cells.

Separation of vitamin $B_{12}$ from the cells and its purification can be carried out by various means.

For example, when it is to be separated from the cells in the form of a coenzyme vitamin $B_{12}$ (5,6-dimethylbenzimidazole cobamide coenzyme), crushed cells obtained by crushing the collected microbial cells or the cellular membranes by a physical means such as milling or by an ultrasonicating means are extracted in the dark with a solvent such as an alcohol (e.g., methanol, ethanol or isopropanol) or pyridine. When it is to be separated in the form of hydroxocobalamin from the cells, the extract of the coenzyme vitamin $B_{12}$ obtained as above is exposed to light to convert it to hydroxocobalamin. When it is desired to separate it in the form of cyanocobalamin from the cells, the cells are extracted with the aforesaid solvent in the presence of a cyanide salt such as sodium cyanide and potassium cyanide.

According to another embodiment, a vitamin $B_{12}$-containing liquid containing impurities, for example a cell crushed liquid obtained by crushing the cellular membranes as above, or an extract obtained by extracting the cells or its crushed product with the above-exemplified extracting solvent, is subjected to adsorption-elution treatment using adsorbents, whereby vitamin $B_{12}$ can be purified.

According to this embodiment in which an adsorbent is used, the aforesaid vitamin $B_{12}$-containing liquid is contacted with a copolymer resin having a surface area of at least about 700 m$^2$/g and derived from divinylbenzene, styrene or its functional derivative, for example a functional derivative such as a $C_1$–$C_6$ alkyl-substituted derivative (e.g., methylstyrene, ethylstyrene, dimethylstyrene or propylstyrene) and an unsaturated alkyl ester of an aromatic polycarboxylic acid, expressed by the following formula

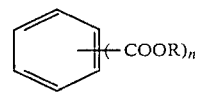

wherein R represents a $C_3$–$C_{10}$ unsaturated alkyl group having a carbon-carbon double bond, and n is 2 or 3, for example di- or tri-$C_3$–$C_{10}$ alkenyl esters such as triisopropenyl 1,2,4-benzenetricarboxylate and diisopropenyl terephthalate to cause adsorption of vitamin $B_{12}$ on the resin, and eluting the adsorbed vitamin $B_{12}$ with an eluent, and collecting active eluate fractions. The adsorption-elution can be performed batchwise or by a column chromatographic method. Adsorption can be carried out, for example, at a pH of about 5 to about 8, preferably about 7, and at a temperature of about 10° C. to about 30° C. After the adsorption treatment, the resin may, if desired, be washed, and then eluated to give active eluate fractions.

The washing treatment may be performed by, for example, using hydrous alcohols having low concentrations, for example, 5% aqueous methanol, 2% aqueous ethanol, and 1% aqueous isopropanol. Ordinary eluents can be used as the eluent. For example, the eluent is an aqueous solution of an eluent selected from the group consisting of lower alcohols, acids, alkalies and salts. Specific examples of the eluents include lower alcohols such as methanol, ethanol and isopropanol, acids such as phosphoric acid, acetic acid, boric acid and hydrochloric acid, alkalies such as sodium hydroxide, ammonium phosphate and ammonium hydroxide, and salts such as sodium carbonate, sodium acetate, sodium phosphate and potassium phosphate. The eluent can also be properly selected according to the kinds and amounts of impurities, the kind of the adsorbent resin, etc. Aqueous solutions of lower alcohols are preferred, and hydrous alcohols having an alcohol content of less than about 50%, for example 25–50% methanol, 15–40% ethanol and 6–20% isopropanol can be cited. The eluting operation can be carried out at room temperature. Heating or cooling may be carried out if desired, although it is not particularly necessary. For example, the operating temperature is about 30° to about 60° C.

Active eluted fractions are collected, and as required may be subjected to concentration, recrystallization, etc.

According to still another embodiment in which an adsorbent is used, the vitamin $B_{12}$-containing liquid containing impurities described in the aforesaid embodiment may be contacted with a divinylbenzene/styrene copolymer resin having a most frequent pore diameter [determined by the method described at pages 31–73 of "Porous Material", written by Renichi Kondo, published on Sep. 5, 1973 by Gihodo Company, Japan] of at least about 200 Å, preferably at least about 250 Å, for example about 200 to about 1200 Å, and a pore volume of more than 0.6 ml/g, for example above 0.6 ml/g and up to about 1.2 ml/g, to cause adsorption of vitamin $B_{12}$ on the resin, followed by eluting the adsorbed vitamin $B_{12}$ with an eluent and collecting active eluted fractions.

As the adsorbent resin used in the above procedure, Diaion HP-10, HP-20, HP-30, HP-40 and HP-50 (tradenames for products of Mitsubishi Chemical Co., Ltd., Japan) are commercially available. Such resins can also be produced by copolymerizing divinylbenzene with styrene or its functional derivative such as those exemplified hereinabove.

The adsorption and elution operations and conditions therefor may be the same as described hereinabove. The washing treatment optionally carried out after adsorption, and the elution treatment can also be carried out by the same operations and under the same conditions as described with respect to the first-mentioned embodiment.

In the practice of the process of this invention, vitamin $B_{12}$ is recovered from the microbial cells as described above, and if desired, can then be purified. Other purifying means may also be used. For example, there can be employed extraction with phenol, adsorption with activated carbon, adsorption with ion-exchange resins or cellulose, and column chromatography in suitable combinations.

The following Examples illustrate the present invention in greater detail.

EXAMPLE 1

Six milliliters of a culture medium A containing 25 g of glucose, 20 g of corn steep liquor, 3 g of $NH_4NO_3$, 0.4 g of $KH_2PO_4$, 1.5 g of $Na_2HPO_4.12H_2O$, 0.5 g of $MgSO_4.7H_2O$, 30 mg of $Co(NO_3)_2.6H_2O$, 10 mg of $ZnSO_4.7H_2O$, 5 mg of $MnSO_4.4H_2O$, 50 μg of $CuSO_4.5H_2O$, 10 μg of $(NH_4)_6Mo_7O_{24}.4H_2O$, 5 mg of calcium pantothenate and 10 mg of $CaCO_3$ per liter of water was put in a 200 ml Erlenmeyer flask and sterilized, and *Propionibacterium shermanii* IFO 12391 was inoculated in the culture medium. This microorganism strain was cultivated under stationary conditions for 4 days at 30° C.

Separately, 2 liters of a culture medium B containing 10 g of glucose, 80 g of corn steep liquor, 16 g of $(NH_4)_2SO_4$, 0.4 g of $KH_2PO_4$, 1.5 g of $Na_2HPO_4.12H_2O$, 0.5 g of $MgSO_4.7H_2O$, 30 mg of $Co(NO_3)_2.6H_2O$, 10 mg of $ZnSO_4.7H_2O$, 5 mg of $MnSO_4.4H_2O$, 50 μg of $CuSO_4.5H_2O$, 10 μg of $(NH_4)_6Mo_7O_{24}.4H_2O$ and 10 mg of calcium pantothenate per liter of water was fed into a 5-liter fermentor and sterilized. Sixty milliliters of the above seed strain broth was inoculated in the culture medium and its cultivation was started.

The cultivation was carried out at 30° C. while blowing $N_2$ gas and automatically controlling the pH of the culture broth using 5N sodium hydroxide. A pump for supplying a 60% (W/V) solution of glucose was designed to be operated automatically in relation to the motion of a pump for supplying sodium hydroxide. The concentration of glucose remaining in the culture broth was maintained at about 10 g/liter. On the fourth day of cultivation, 5,6-dimethylbenzimidazole was added in an amount of 10 mg/liter of the culture broth, and then the cultivation was continued for 3 days. At this time, the amount of the culture broth reached 3.2 liters. The amount of 5N sodium hydroxide used was 650 ml, and the amount of the 60% glucose solution used was 650 ml. The amount of vitamin $B_{12}$ per liter of the culture broth was 43 mg when determined by a customary bioassay method using *Lactobacillus leichmannii* IFO 3376. In other words, 138 mg of vitamin $B_{12}$ was obtained per 410 g of glucose used.

COMPARATIVE EXAMPLE 1

650 ml of a 60% (W/V) glucose solution was added to 2-liters of the culture medium B shown in Example 1, and the mixture was charged into a 5-liter fermentor and sterilized. Sixty milliliters of the same seed strain broth as used in Example 1 was inoculated in the fermentor, and its cultivation was started. The cultivation was carried out at 30° C. while blowing $N_2$ gas into the fermentor and automatically controlling the pH of the culture broth using 5N sodium hydroxide. There was an induction period of 2 days for growth, and therefore, on the sixth day of cultivation, 5,6-dimethylbenzimidazole was added to the culture broth in an amount of 10 mg/liter of culture broth. Thereafter, the cultivation was continued for 3 days. The amount of the culture broth at this time was 3.0 liters, and the amount of sodium hydroxide used was 400 ml. The amount of vitamin $B_{12}$ per liter of the resulting culture broth was 26 mg when it was determined by a customary bioassay method using *Lactobacillus leichmannii* IFO 3376. This means that only 78 mg of vitamin $B_{12}$ was produced per 410 g of glucose used.

EXAMPLE 2

Cultivation was carried out in the same way as in Example 1 except that *Propionibacterium freudenreichii* IFO 12424 was used instead of *Propionibacterium shermanii* IFO 12391. When the cultivation was carried out for 7 days in a 5-liter fermentor, the amount for the culture broth was 3.1 liters, and the amount of sodium hydroxide used was 600 ml. The amount of the 60% glucose solution used was also 600 ml. The amount of vitamin $B_{12}$ obtained per liter of the culture broth was 29 mg when it was determined by a customary biaoassay method using *Lactobacillus leichmannii* IFO 3376. This means that 90 mg of vitamin $B_{12}$ was produced per 380 mg of glucose used.

COMPARATIVE EXAMPLE 2

600 ml of a 60% (W/V) glucose solution was added to 2 liters of the culture medium shown in Example 1, and the mixture was charged into a 5-liter fermentor and sterilized. Then, 60 ml broth of a seed strain, *Propionibacterium freudenreichii* IFO 12424 shown in Example 2, was inoculated, and its cultivation was started. The cultivation was carried out at 30° C. while blowing $N_2$ gas into the fermentor and automatically controlling the pH of the cultivation product using 5N sodium hydroxide. Since there was an induction period of 2 days for growth, 5,6-dimethylbenzimidazole was added in an amount of 10 mg/liter of the culture broth on the sixth day of cultivation. Then, the cultivation was continued for 3 days. At this time, the amount of the culture broth was 2.9 liters, and the amount of sodium hydroxide used was 420 ml. The amount of vitamin $B_{12}$ per liter of the culture broth was 16 mg when it was determined by a customary bioassay method using *Lactobacillus leichimannii* IFO 3376. This means that only 46 mg of vitamin $B_{12}$ was produced from 380 g of glucose used.

EXAMPLE 3

Cultivation was carried out in the same way as in Example 1 except that *Propionibacterium shermanii* NOC 11012 was used instead of *Propionibacterium shermanii* IFO 12391. When the cultivation was carried out for 7 days in a 5-liter fermentor, the amount of the cultivation product was 3.3 liters. The amount of 5N sodium hydroxide used was 660 ml, and the amount of the 60% glucose solution used was also 660 ml. The amount of vitamin $B_{12}$ obtained per liter of the cultivated product was 65 mg when it was determined by a customary bioassay method using *Lactobacillus leichimannii* IFO 3376. This means that 215 mg of vitamin $B_{12}$ was produced per 416 g of glucose used.

COMPARATIVE EXAMPLE 3

660 ml of a 60% (W/V) solution of glucose was added to 2 liters of the culture medium B shown in Example 1 and the mixture was charged into a 5-liter fermentor and sterilized. Then, 60 ml broth of a seed strain, *Propionibacterium shermanii* NOC 11012 shown in Example 3 was inoculated in the fermentor and its cultivation was started. The cultivation was carried out at 30° C. while blowing $N_2$ gas into the fermentor and automatically controlling the pH of the culture broth using 5N sodium hydroxide. Since there was an induction period of two days for growth, 5,6-dimethylbenzimidazole was added in an amount of 10 mg/liter of the culture broth on the sixth day of cultivation. Then, the cultivation was continued for 3 days. At this time, the amount of the culture broth was 3.0 liters, and the amount of sodium hydroxide used was 400 ml. The amount of vitamin $B_{12}$ obtained per liter of the culture broth was 40 mg when it was determined by a customary bioassay method using *Lactobacillus leichimannii* IFO 3376. This means that 120 mg of vitamin $B_{12}$ was produced per 416 g of glucose used.

EXAMPLE 4

Cultivation was carried out in the same way as in Example 1 except that *Propionibacterium shermanii* NOC 11011 was used instead of *Propionibacterium shermanii* IFO 12391. When the cultivation was performed for 7 days in a 5-liter fermentor, the amount of the culture broth was 3.2 liters, and the amount of 5N sodium hydroxide used was 630 ml. The amount of the 60% solution of glucose used was also 630 ml. The amount of vitamin $B_{12}$ obtained per liter of the culture broth was 48 mg when it was determined by a customary bioassay method using *Lactobacillus leichimannii* IFO 3376. This means that 154 mg of vitamin $B_{12}$ was produced per 398 g of glucose used.

COMPARATIVE EXAMPLE 4

630 ml of a 60% (W/V) solution of glucose was added to 2 liters of the culture medium B shown in Example 1 and the mixture was charged into a 5-liter fermentor and sterilized. Then, 60 ml of a seed strain, *Propionibacterium shermanii* NOC 11011 shown in Example 5, was inoculated in the fermentor, and its cultivation was started. The cultivation was carried out at 30° C. while blowing $N_2$ gas into the fermentor and automatically controlling the pH of the culture broth using 5N sodium hydroxide. Since there was an induction period of 2 days for growth, 5,6-dimethylbenzimidazole was added in an amount of 10 mg/liter of the culture broth on the sixth day of the cultivation. Thereafter, the cultivation was continued for 3 days. At this time, the amount of the culture broth was 2.0 liters, and the amount of sodium hydroxide used was 390 ml. The amount of vitamin $B_{12}$ obtained per liter of the culture broth was 29 mg when it was determined by a customary bioassay method using *Lactobacillus leichimannii* IFO 3376. This means that 84 mg of vitamin $B_{12}$ was produced per 398 g of glucose used.

EXAMPLE 5

Cultivation was carried out in the same way as in Example 1 except that *Propionibacterium freudenreichii* NOC 11013 was used instead of *Propionibacterium shermanii* IFO 12391. When the cultivation was carried out for 7 days in a 5-liter fermentor, the amount of the culture broth was 3.3 liters. The amount of 5N sodium hydroxide used was 680 ml, and the amount of the 60% glucose solution used was 680 ml. The amount of vitamin $B_{12}$ obtained per liter of the culture broth was 42 mg when it was determined by a customary bioassay method using *Lactobacillus leichimannii* IFO 3376. This means that 139 mg of vitamin $B_{12}$ was produced per 428 g of glucose used.

COMPARATIVE EXAMPLE 5

680 ml of a 60% (W/V) solution of glucose was added to 2 liters of the culture medium B shown in Example 1, and the mixture was charged into a 5-liter fermentor and sterilized. Then 60 ml of a broth of a seed strain, *Propionibacterium freudenreichii* NOC 11013 shown in Example 5, was inoculated in the fermentor and its cultivation was started. The cultivation was carried out at 30° C. while blowing $N_2$ gas into the fermentor and automatically controlling the pH of the culture broth using 5N sodium hydroxide. Since there was an induction period of 2 days for growth, 5,6-dimethylbenzimidazole was added in an amount of 10 mg/liter on the sixth day of cultivation. Then, the cultivation was continued for 3 days. At this time, the amount of the cultivation product was 3.0 liters, and the amount of sodium hydroxide used was 430 ml. The amount of vitamin $B_{12}$ obtained per liter of the cultivation product was 24 mg when it was determined by a customary bioassay method using *Lactobacillus leichimannii* IFO 3376. This means that 72 mg of vitamin $B_{12}$ was produced per 428 g of glucose used.

EXAMPLE 6

Sixty milliliters of a culture medium A containing 12.5 g of fructose, 12.5 g of glucose, 20 g of corn steep liquor, 3 g of $NH_4NO_3$, 0.4 g of $KH_2PO_4$, 1.5 g of $Na_2HPO_4.12H_2O$, 0.5 g of $MgSO_4.7H_2O$, 30 mg of $Co(NO_3)_2.6H_2O$, 10 mg of $ZnSO_4.7H_2O$, 5 mg of $MnSO_4.4H_2O$, 50 μg of $CuSO_4.5H_2O$, 10 μg of $(NH_4)_6Mo_7O_{24}.4H_2O$, 5 mg of calcium pantothenate and 10 g of $CaCO_3$ per liter of water was put in a 200 ml Erlenmeyer flask and sterilized, and *Propionibacterium shermanii* IFO 12391 was inoculated. The cultivation was carried out for 4 days at 30° C. under stationary conditions.

Separately, 2 liters of a culture medium B containing 5 g of fructose, 5 g of glucose, 80 g of corn steep liquor, 16 g of $(NH_4)_2SO_4$, 0.4 g of $KH_2PO_4$, 1.5 g of $Na_2HPO_4.12H_2O$, 0.5 g of $MgSO_4.7H_2O$, 30 mg of $Co(NO_3)_2.6H_2O$, 10 mg of $ZnSO_4.7H_2O$, 5 mg of $MnSO_4.4H_2O$, 50 μg of $CuSO_4.5H_2O$, 10 μg of $(NH_4)_6Mo_7O_{24}.4H_2O$ and 10 mg of calcium pantothenate was charged into a 5-liter fermentor and sterilized. Then, 60 ml of the aforesaid seed strain was inoculated in the fermentor and its cultivation was started.

The cultivation was carried out at 30° C. while blowing $N_2$ gas into the fermentor and automatically controlling the pH of the culture broth using 5N sodium hydroxide. A pump for supplying an aqueous solution containing 30% (W/V) each of glucose and fructose was designed to operate automatically in response to the motion of a pump for supplying sodium hydroxide. The concentration of each of fructose and glucose remaining in the culture broth was maintained at about 5 g/liter. On the fourth day of cultivation, 5,6-dimethylbenzimidazole was added in an amount of 10 mg/liter of the culture broth, and then the cultivation was continued for 3 days. At this time, the amount of the culture broth was 3.2 liters, and the amount of 5N sodium hydroxide used was 640 ml. The amount of the aqueous solution containing 30% of fructose and 30% of glucose was 640 ml. The amount of vitamin $B_{12}$ obtained per liter of the culture broth was 52 mg when it was determined by a customary bioassay method using *Lactobacillus leichmannii* IFO 3376. This means that 166 mg of vitamin $B_{12}$ was produced per 202 g of fructose and 202 g of glucose.

EXAMPLE 7

Cultivation was carried out in the same way as in Example 6 except that *Propionibacterium shermanii* NOC 11012 was used instead of *Propionibacterium shermanii* IFO 12391. When the cultivation was carried out for 7 days in a 5-liter fermentor, the amount of the culture broth was 3.2 liters, and the amount of sodium hydroxide used was 650 ml. The amount of the aqueous solution containing 30% (W/V) each of fructose and glucose was also 650 ml. The amount of vitamin $B_{12}$ obtained per liter of the culture broth was 75 mg when it was determined by a customary bioassay method using *Lactobacillus leichimannii* IFO 3376. This means that 240 mg of vitamin $B_{12}$ was produced per 205 g of fructose and per 205 g of glucose.

EXAMPLE 8

(1) Derivation of a propionic acid-resistant strain (*Propionibacterium shermanii* NOC 11012)

Ultraviolet light was irradiated for 2 minutes onto *Propionibacterium shermanii* IFO 12391 from two 15W sterilizing lamps placed at a height 40 cm from the microorganism to subject it to a mutation treatment.

Then, the microorganism was cultivated for 20 days in a plate culture medium obtained by adding 20 g/liter of propionic acid (which was above the minimum growth inhibitory concentration for the parent strain) to a minimum culture medium shown in Table 1, and the growth colonies were collected.

TABLE 1

| Minimum culture medium (plate) | |
|---|---|
| Glucose | 50 g |
| Corn steep liquor | 40 g |
| $NH_4NO_3$ | 3 g |

TABLE 1-continued

| Minimum culture medium (plate) | |
|---|---|
| $Na_2HPO_4.12H_2O$ | 1.5 g |
| $KH_2PO_4$ | 0.4 g |
| $MgSO_4.7H_2O$ | 0.5 g |
| $MnSO_4.4H_2O$ | 5 mg |
| $FeSO_4.7H_2O$ | 10 mg |
| $ZnSO_4.7H_2O$ | 10 mg |
| $CuSO_4.5H_2O$ | 0.05 mg |
| $(NH_4)_6Mo_7O_{24}.4H_2O$ | 0.01 mg |
| $Co(NO_3)_2.6H_2O$ | 15 mg |
| Calcium pantothenate | 5 mg |
| $CaCO_3$ | 10 g |
| Agar | 20 g |
| Deionized pure water | 1 liter |

The resulting colonies were cultivated for 5 days in a liquid culture medium obtained by adding 20 g/liter of propionic acid (above the minimum inhibitory concentration for the parenteral strain) to the minimum culture medium shown in Table 2. This cultivation was repeated ten times, and colonies which did not undergo growth inhibition were collected.

TABLE 2

| Minimum culture medium (liquid) | |
|---|---|
| Glucose | 25 g |
| Corn steep liquor | 40 g |
| $NH_4NO_3$ | 3 g |
| $Na_2HPO_4.12H_2O$ | 1.5 g |
| $KH_2PO_4$ | 0.4 g |
| $MgSO_4.7H_2O$ | 0.5 g |
| $MnSO_4.4H_2O$ | 5 mg |
| $FeSO_4.7H_2O$ | 10 mg |
| $ZnSO_4.7H_2O$ | 10 mg |
| $CuSO_4.5H_2O$ | 0.05 mg |
| $(NH_4)_6Mo_7O_{24}.4H_2O$ | 0.01 mg |
| $Co(NO_3)_2.6H_2O$ | 15 mg |
| Calcium pantothenate | 5 mg |
| $CaCO_3$ | 10 g |
| Deionized pure water | 1 liter |
| Initial pH | 7.0 |

(2) Test for evaluating vitamin $B_{12}$ productivity

Two hundred milliliters of a culture medium having the composition shown in Table 3 was placed in a 500 ml Erlenmeyer flask, and sterilized by steaming under pressure at 120° C. for 10 minutes. The culture broth of each of the parenteral strain cultivated for 5 days in the culture medium shown in Table 2, and the mutant (*Propionibacterium shermanii* NOC 11012) was inoculated in an amount of 2 ml in the aforesaid sterilized medium and cultivated at 30° C. for 7 days under stationary conditions. During the cultivation, the pH was intermittently adjusted to about 7 by using 20% $NaCO_3$ once a day.

TABLE 3

| Composition of the culture medium | |
|---|---|
| Glucose | 50 g |
| Corn steep liquor | 40 g |
| $NH_4NO_3$ | 3 g |
| $Na_2HPO_4.12H_2O$ | 1.5 g |
| $KH_2PO_4$ | 0.4 g |
| $MgSO_4.7H_2O$ | 0.5 g |
| $MsSO_4.4H_2O$ | 5 mg |
| $FeSO_4.7H_2O$ | 10 mg |
| $ZnSO_4.7H_2O$ | 10 mg |
| $CuSO_4.5H_2O$ | 0.05 mg |
| $(NH_4)_6Mo_7O_{24}.H_2O$ | 0.01 mg |
| $Co(NO_3)_2.6H_2O$ | 15 mg |
| Calcium pantothenate | 5 mg |
| 5,6-Dimethylbenzimidazole | 10 mg |
| $CaCO_3$ | 10 mg |
| Deionized pure water | 1 liter |

TABLE 3-continued

| Composition of the culture medium | |
|---|---|
| Initial pH | 7.0 |

Vitamin $B_{12}$ was determined as follows: To 0.3 ml of the culture broth were added 4.5 ml of an acetate buffer (pH 4.7) and 1 ml of KCN solution (1 g/liter), and the mixture was boiled for 15 minutes at more than 85° C. to extract vitamin $B_{12}$ from the cells by hot water and simultaneously convert it to a stable CN-form. It was bioassayed by using *Lactobacillus leichmannii* IFO 3376 which is a vitamin $B_{12}$-requiring strain. Cyanocobalamin was used as a standard.

The results for the parent strain and the five mutants (propionic acid-resistant strains indicated as $PA^r$) are shown in Table 4. The amounts of vitamin $B_{12}$ produced by the mutants were twice as large as that by the parental strain.

TABLE 4

| Comparison of the amounts of vitamin $B_{12}$ produced | |
|---|---|
| Parental strain | 10 mg/liter |
| Mutants | |
| $PA^r$ 1 | 21 |
| $PA^r$ 2 | 21 |
| $PA^r$ 3 | 20 |
| $PA^r$ 4 | 21 |
| $PA^r$ 5 | 22 |

EXAMPLE 9

Propionic acid-resistant strains (*Propionibacterium freudenreichii*, NOC 11013) were derived from the parental strain *Propionibacterium freudenreichii* IFO 12424 in the same way as in Example 8, and the vitamin $B_{12}$ productivities of these strains were evaluated, and the results are shown in Table 5. It is seen that the amounts of vitamin $B_{12}$ produced by the mutants were twice as large as that produced by the parental strain.

TABLE 5

| Comparison of the amounts of vitamin $B_{12}$ produced | |
|---|---|
| Parental strain | 7 mg/liter |
| Mutants | |
| $PA^r$ 1 | 15 |
| $PA^r$ 2 | 13 |
| $PA^r$ 3 | 14 |
| $PA^r$ 4 | 16 |
| $PA^r$ 5 | 14 |

REFERENTIAL EXAMPLE 1

The mutant, *Propionibacterium shermanii* NOC 11011 (FERM BP-85), used in Example 3 was obtained by the following procedure.

A culture broth of *Propionibacterium shermanii* IFO 12391 was put in an amount of 6.5 ml in a Petri dish, and irradiated with two 15 W ultraviolet lamps placed at a height of 40 cm. Eight milliliters of the culture medium A shown in Example 1 was placed in a test tube having an outside diameter of 17 mm and sterilized. Then, 2 ml of the culture broth irradiated with ultraviolet light as above was added to the culture medium, and allowed to stand at 30° C. Every 1 to 7 days, 8 ml of the culture broth was collected, and 8 ml of the culture medium A was additionally supplied. This procedure was repeated 26 times. The culture broth finally obtained by repeated cultivation was diluted and inoculated in a plate culture medium obtained by adding 2% of agar to the culture medium A, followed by cultivation at 30° C. for 2 weeks. One hundred colonies thus obtained were respectively transferred to 100 test tubes having an outside diameter of 17 mm and each containing 10 ml of the sterilized culture medium A, and cultivated for 5 days. Strains which showed good sedimentation of the cells were separated, and named NOC 11011 strain.

What is claimed is:

1. A process for producing vitamin $B_{12}$ by a fermentation technique, which comprises cultivating a vitamin $B_{12}$-producing microorganism belonging to the genus Propionibacterium in a culture medium containing a carbon source and a nitrogen source, and collecting vitamin $B_{12}$ accumulated in cells of the microorganism, wherein
    (1) the cultivation is carried out while adding an alkali at suitable times to the cultivation system so that during the cultivation, the cultivation system is maintained at a pH in the range of about 5 to about 7.5, and
    (2) the cultivation is carried out while adding a carbon source portionwise to the cultivation system nearly at the same time as the addition of the alkali, the amount of the added carbon source being about 50 g to about 300 g per gram of the added alkali.

2. The process of claim 1 wherein the carbon source added in (2) is at least one member selected from the group consisting of hydrocarbons, sugars and alcohols.

3. The process of claim 1 wherein the carbon source added in (2) is fructose or a fructose-containing carbon source.

4. The process of claim 1 wherein the carbon source added in (2) is a mixture of fructose and glucose, or a carbon source containing fructose and glucose.

5. The process of claim 1 wherein the amount of the carbon source added in (2) is such that the amount of the carbon source remaining in the cultivation system does not exceed about 60 g/liter of the culture medium.

6. The process of claim 1 wherein the portionwise addition of the carbon source in (2) is carried out by operating a pump for supplying the carbon source in relation to the motion of a pump for supplying the alkali in (1).

7. The process of claim 1 wherein the vitamin $B_{12}$-producing microorganism is a member selected from the group consisting of Propionibacterium shermanii and, Propionibacterium freudenreichii.

8. The process of claim 1 wherein the vitamin $B_{12}$-producing microorganism is a member selected from the group consisting of Propionibacterium shermanii NOC 11011, propionic acid-resistant Propionibacterium shermanii NOC 11012, and propionic acid-resistant Propionibacterium freudenreichii NOC 11013.

9. The process of claim 1 wherein the vitamin $B_{12}$-producing microorganism is a propionic acid-resistant, vitamin $B_{12}$-producing microorganism of the genus Propionibacterium.

10. A propionic acid-resistant, vitamin $B_{12}$-producing microorganism of the genus Propionibacterium.

11. The microorganism of claim 10 which is a member selected from the group consisting of *Propionibacterium shermanii* and *Propionibacterium freudenreichii*.

12. A propionic acid-resistant, vitamin $B_{12}$-producing microorganism which is a member selected from the group consisting of *Propionibacterium shermanii* NOC 11012 and *Propionibacterium freudenreichii* NOC 11013.

* * * * *